United States Patent [19]

Hellwig et al.

[11] Patent Number: 5,206,304

[45] Date of Patent: Apr. 27, 1993

[54] VULCANIZABLE RUBBER MIXTURES CONTAINING BIS-(2,4-ORGANYLTHIO-TRIAZINE-6-YL) POLYSULFIDES

[75] Inventors: Georg Hellwig, Freigericht; Reinhard Stober, Hasselroth; Christoph Klatte; Ulrich Deschler, both of Hanau; Siegfried Wolff, Bornheim; Udo Görl, Meckenheim, all of Fed. Rep. of Germany

[73] Assignee: Degussa Aktiengesellschaft, Fed. Rep. of Germany

[21] Appl. No.: 751,586

[22] Filed: Aug. 22, 1991

Related U.S. Application Data

[63] Continuation of Ser. No. 369,239, Jun. 22, 1989, abandoned.

[30] Foreign Application Priority Data

Jun. 22, 1988 [DE] Fed. Rep. of Germany ....... 3820969

[51] Int. Cl.$^5$ .............................. C08C 19/20
[52] U.S. Cl. ................ 525/329.3; 525/331.8; 525/332.6; 525/333.9; 525/349
[58] Field of Search ................ 52/331.8, 332.6, 329.3, 52/333.9, 333.1, 333.2

[56] References Cited

U.S. PATENT DOCUMENTS

| | | |
|---|---|---|
| 3,366,598 | 1/1968 | Westlinning . |
| 3,775,366 | 11/1973 | Wolff . |
| 3,801,537 | 4/1974 | Westlinning ................ 525/348 |
| 4,517,336 | 5/1985 | Wolff ................ 524/571 |

*Primary Examiner*—Christopher Henderson

[57] ABSTRACT

Bis(2,4-organylthio-s-triazine-6-yl) polysulfides of the general Formula (I)

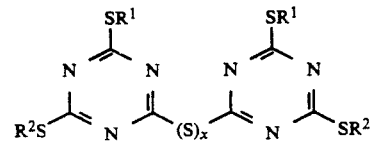

prepared from compounds of the general formula (II)

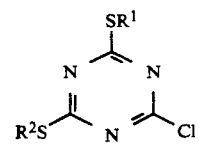

and from an ammonium or alkali polysulfide and the use of such compounds as accelerators in vulcanizable rubber mixtures.

5 Claims, No Drawings

VULCANIZABLE RUBBER MIXTURES CONTAINING BIS-(2,4-ORGANYLTHIO-TRIAZINE-6-YL) POLYSULFIDES

This is a continuation of application Ser. No. 07/369,239, filed on Jun. 22, 1989, now abandoned.

The present invention relates to binucleate s-triazine compounds which are linked via a poly-sulfide chain, a method for their preparation and vulcanizable rubber mixtures containing them.

BACKGROUND OF THE INVENTION

Binucleate s-triazine compounds with a poly-sulfide chain are known e.g. from German patent DE-PS No. 1 669 954, U.S. Pat. No. 3,923,724 and U.S. Pat. No. 4,621,121. These publications concern bis(2-ethylamino-4-diethylamino-s-triazine-6-yl) disulfide and the corresponding tetrasulfide, which are used in vulcanizable rubber mixtures as vulcanization accelerators.

SUMMARY OF THE INVENTION

The object of the present invention is to provide vulcanization accelerators which simplify the processing of rubber mixtures as a result of higher scorch times and curing times.

These and other objects are achieved by bis(2,4-organylthio-s-triazine-6-yl) polysulfides of the general formula (I)

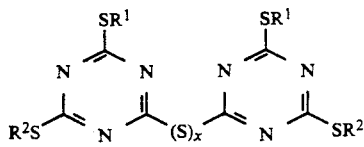

in which: $R^1$, $R^2$ are identical or different and represent hydrogen, branched or unbranched alkyl with 1–4 carbon atoms, $C_3$–$C_8$ cycloalkyl, especially cyclohexyl, phenyl or also 2-hydroxyethyl, 3-hydroxypropyl, 2-hydroxypropyl, $(S)_x$ is a polysulfide chain with 2–10 sulfur atoms ($2 \leq x \leq 10$) and the individual polysulfides are present in such concentrations that the statistical mean value of x ($\bar{x}$) assumes whole or fractional numerical values of 2 to 5 and especially 4.

The invention also provides a method of preparing the foregoing compounds in which an s-triazine compound of the general formula (II)

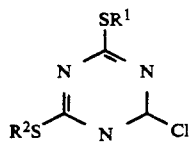

in which $R^1$ and $R^2$ have the meanings indicated above, is reacted with a polysulfide compound of the general formula (III)

$Me_2S_x$, in which Me stands for the ammonium cation or an alkali metal cation, especially sodium or potassium, and $S_{\bar{x}}$ has the value indicated above, and especially $\bar{x}$ is 4, in a molar ratio of 2:1 to 2:1.2. The reaction is carried out in an organic solvent, preferably a polar solvent, or a mixture of solvent with water at a temperature of 0° C. to the boiling point of the organic solvent. The organic solvent especially may be tetrahydrofuran (THF), 1,2 dimethoxy ethane or ketones such as e.g. acetone, methylethyl ketone and isobutylmethyl ketone. When the reaction is complete, the product is separated and dried.

The following general procedure is used in carrying out this process: The starting material according to Formula (II) is dissolved in the organic solvent and the solution is placed in a reaction vessel, then the polysulfide according to Formula (III), preferably disodium tetrasulfide, is added with vigorous agitation either in a finely powdered form or dissolved in water and the reaction is allowed to proceed, preferably at temperatures of 20° to 50° C. The water component of the reaction mixture should not exceed 2 to 40% by weight.

It is also important for the selection of the organic solvent that the desired product precipitates as a solid, so that it can be e.g. filtered off easily.

The s-triazine derivatives used as starting materials can be obtained e.g. according to the disclosure of French Pat. No. 1,592,489.

In a preferred embodiment, the reaction is allowed to proceed in the presence of a known phase transfer catalyst which corresponds to the following formula scheme:

$[R_nNH_{4-n}]^+X^-$, in which $n = 1, 2, 3$ or $4$
$[R_pPH_{4-p}]^+X^-$, in which $p = 3$ or $4$
$[R'C_5H_4NR'']^+X^-$, in which $C_5H_4N$ is a pyridine ring, and $[R_1R_2R_3S]^+X^-$, in which X represents halogen, hydroxide or hydrogen sulfate ($HSO_4^-$), R represents an alkyl group with 1–18 carbon atoms, an alkenyl group with 1–18 carbon atoms, a phenyl group or a benzyl group although compounds 1 and 2 do not contain more than one of these phenyl and benzyl groups, R' represents hydrogen, an alkyl or alkylene group with 1–4 carbon atoms R'' represents an alkyl or alkenyl group with 1–18 carbon atoms, and $R^1$, $R^2$ and $R^3$ represent an alkyl or alkenyl group with 1–18 carbon atoms or a phenyl group.

These catalysts are added in an amount of 0.1–5% by weight in relation to the s-triazine compound of general Formula II.

The compounds of the present invention according to Formula (I) are distinguished in their use as vulcanization accelerators over the known, state-of-the-art bis(2-ethylamino-4-diethylamino-s-triazine-6-yl) tetrasulfides, depending on the rubber type, by a higher Mooney Scorch Time, a clearly longer curing time, an increased degree of cross-linking speed and/or better reversion behavior.

Another disadvantage of some conventional accelerators (e.g. some sulfenamides, thiurams), which can no longer be disregarded, arises from the release of amines during vulcanization which leads, insofar as they are nitrosatible, to the formation of nitrosamines in the vulcanizate. This makes it probable, to the extent that these nitrosamines are toxic, that the possible application of these accelerators will have to be limited in the long run.

The use of the compounds according to Formula (I) claimed in accordance with the present invention comprises the known, state-of-the-art rubber mixtures based on natural rubber (NR), isoprene rubber (IR), butadiene rubber (BR), styrene-butadiene rubber (SBR), isobutylene-isoprene rubber (IIR), ethylene-propylene terpolymer (EPDM), nitrile rubber (NBR), halogen-containing rubbers and also epoxidized natural rubbers (ENR) as well as blends of these rubbers. The use of the compounds of the present invention in the case of reversion-prone rubber types such as e.g. natural rubber, isoprene rubbers and butadiene rubbers as well as their blends with each other or with other rubbers has special significance.

In accelerated sulfur vulcanization, the bis(2,4-organylthio-s-triazine-6-yl) polysulfides of the present invention are added as accelerators in amounts of 0.01 to 10 parts, preferably 0.1 to 5 parts, relative to 100 parts rubber with sulfur contents of 0.1 to 10 parts per 100 parts of rubber. A molar ratio of the accelerators of the invention to sulfur ($S_8$) of 1:0.5 to 1.5 is preferred. In order to achieve a certain variation spread of the vulcanization kinetics, it can be advantageous to add 2 or more bis(2,4-organylthio-s-triazine-6-yl) polysulfides to the mixture, in which instance the substitution should be performed on a molar basis in order to conform to the above-mentioned concentrations of accelerator, especially the preferred accelerator/sulfur ratio.

It can also be advantageous for kinetic reasons to use bis(2,4-organylthio-s-triazine-6-yl) polysulfide in a mixture with conventional accelerators such as e.g. sulfenamides and thiurams. These steps are occasionally at the expense of the reversion resistance in comparison to the pure bis(2,4-organylthio-s-triazine-6-yl) polysulfide vulcanizates.

Conversely, it can be positive as regards the reversion behavior if conventional accelerators are partially replaced by bis(2,4-organylthio-s-triazine-6-yl) polysulfides.

A further considerable effect o the incubation time can be achieved in rubber mixtures by using the compounds of the present invention in combination with commercially available antiscorchers or retarders such as e.g. Santoguard PVI (N-(cyclohexylthio)-phthalimide), Vulkalent E (N-phenyl-N-(trichloromethylsulfenyl)-benzene sulfinamid) as well as substances such as those described in South African Pat. Nos. 87/1767 and 87/1768 and in U.S. Pat. No. 3,546,185. Their increasing addition results in a linear rise of the incubation time of mixtures containing bis(2,4-organylthio-s-triazine-6-yl) polysulfides.

The antiscorchers, especially the ones cited above, and the compounds of the invention according to general Formula I are used in a molar ratio of 0.5 to 1.5:1, especially 0.8 to 1.2:1 at a sulfur content of 0.1 to 10 parts by weight, preferably 0.5 to 8 parts by weight relative to 100 parts rubber.

Rubber mixtures which contain the compound of the present invention can also contain other conventional components such as e.g.:

Conventional reinforcing systems, that is, furnace (carbon) blacks, channel blacks, lampblacks, thermal blacks, acetyl blacks, arc blacks, CK blacks, etc. as well as synthetic fillers such as silicic acids, silicates, aluminum oxide hydrates, calcium carbonates and natural fillers such as clays, siliceous chalks, chalks, talcums, etc. as well as silane-modified fillers and their blends in amounts of 5 to 300 parts; the following are especially preferred: silicic acids and silicates as sole fillers in amounts of 5 to 150 parts or in mixtures with carbon black with 10 to 100 parts, relative in each instance to 100 parts rubber, ZnO and stearic acid as promoters of the vulcanization in amounts of 0.5 to 10 parts per 100 parts rubber, Conventionally-used aging, ozone and fatigue protectants such as e.g. IPPD, TMQ as well as waxes as light protectors and their blends, Any softeners desired, such as e.g. aromatic, naphthenic, paraffinic, synthetic softeners and their blends, Optional silanes such as e.g. bis(3-triethoxysilylpropyl) tetrasulfide, 3-chloropropyltriethoxysilane, 3-mercaptopropyltrimethoxysilane,

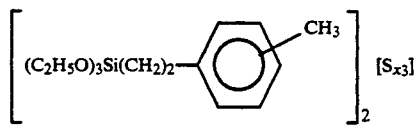

and their blends in an amount of 0.1 to 20 parts, preferably 1 to 10 parts, per 100 parts filler, optionally sulfur in an amount of 0.5 to 4 parts per 100 parts rubber, Optionally, other silanes such as chloropropyltrialkoxysilanes, vinyltrialkoxysilanes and aminoalkyltrialkoxysilanes as well as their blends in an amount of 0.1 to 15 parts, preferably 1 to 10 parts, per 100 parts of fillers such as silicic acids, silicates, clays, etc. carrying silanol groups, Optional dyes and processing aids in the customary amounts.

The bis(2,4-organylthio-s-triazine-6-yl) polysulfides of the present invention includes rubber mixtures such as those customarily used in tire construction and to industrial articles such as e.g. mixtures for conveyor belts, V belts, molded articles, hoses with and without linings, rubber coatings for rollers, jacketings, injection profiles, free-hand articles, foils, shoe soles and top parts, cables, all-rubber tires and their vulcanizates.

The production of the vulcanizable mixtures is carried out according to generally known methods. For example, a kneader with a flowthrough temperature of approximately 60° C. is used.

The rubber mixture, free of sulfur and accelerator, is premixed in such apparatus and then the accelerator and the sulfur, which is optionally likewise provided, and/or an organosilane as adhesive agent is mixed in a second stage.

DETAILED DESCRIPTION OF PREFERRED EMBODIMENTS

The following examples illustrate the invention.

The preparation of bis(2,4-methylthio-s-triazine-6-yl) polysulfide takes place according to the following equation:

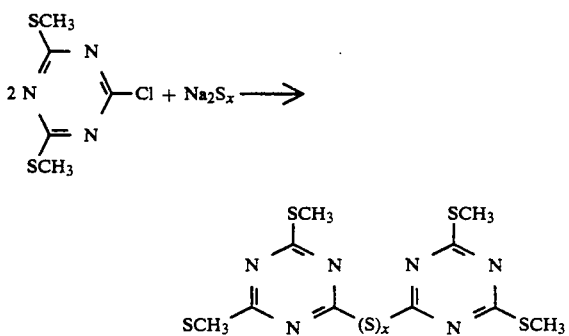

EXAMPLE 1

The apparatus used included a 250 ml multi-necked flask equipped with an agitator, a condenser and a thermometer. The starting materials included
50 mmoles (=10.39 g) 2,4-dimethylmercapto-6-chloro-s-triazine (BMT)
30 mmoles (5.23 g) disodium tetrasulfide
100 ml tetrahydrofuran (THF)

The THF is placed in a receiver at room temperature. The ground BMT is added with agitation. After total dissolution, the finely ground $Na_2S_x$ ($\bar{x} \sim 4$) is added with vigorous agitation (800 rpms.). After up to 5 minutes, a white precipitate is produced and the temperature rises up to 30° C.

The reaction speed can be increased by the addition of 0.3% by weight of a phase transfer catalyst, e.g. benzyltriethyl ammonium chloride (TEBA).

After 60 minutes, the precipitate is removed by suction, washed chloride-free with water and dried over $P_2O_5$.

Yield: 90% polysulfide ($\bar{x} \sim 4$)
Melting point 169°–178° C.

EXAMPLE 2

The apparatus used included a 250 ml multi-necked flask equipped with an agitator, a condenser, a thermometer and a dropping funnel (50 ml).

The starting materials and amounts added are the same as in Example 1. The THF is placed in a flask at room temperature. The ground BMT is added with agitation. After complete dissolution, a solution of $Na_2S_x$ ($\bar{x} \sim 4$) and 25 ml water is added drop-by-drop (agitation speed approximately 800 rpms). A white precipitate is produced after a few minutes and the temperature rises up to approximately 30° C.

Yield: 89% polysulfide ($\bar{x} \sim 4$)
Melting point 160°–180° C.

The identification of the compound produced is performed by

1) Elementary analysis: $C_{10}H_{12}N_6S_8$

|  | C | H | N | S | Cl |
|---|---|---|---|---|---|
| calc.: | 27.26 | 2.74 | 19.07 | 50.93 | 0 |
| observed: | 27.13 | 2.75 | 18.80 | 51.09 | 0.27 |

2) IR spectra

IR (cm$^{-1}$): 3435, 2929, 1499, 1475, 1426, 1323, 1250, 1160, 844, 783

3) NMR

H-NMR (CDCl$_3$, 250 mHz): s. 2.58 ppm
$^{13}$C-NMR (CDCl$_3$), 250 mHz):
ppm: 13.5 (—S—$\underline{C}$H$_3$), 177,187

Test procedures

The physical tests were carried out at room temperature in accordance with the following standard specifications:

|  | measured in |  |
|---|---|---|
| Tensile strength, breaking elongation and tensile modulus in rings 6 mm thick | DIN 53 504 | MPa |
| Reversion | DE-PS 2848559 | % |
| Scorch time | ASTM D 2084 | min. |
| Tear resistance | DIN 53 507 | N/mm |
| Mooney test | DIN 53 523/524 | min. |

The following names and abbreviations are used in the examples, the meaning of which is indicated in the following:

| | |
|---|---|
| Buna 1500: | Styrene-butadiene rubber of the Hüls company |
| RSS: | Ribbed smoked sheet (natural rubber) |
| CORAX ® N 220: | Carbon black, surface (BET) 120 m$^2$/g-Degussa |
| Naftolen ® ZD: | Softener consisting of hydrocarbons |
| Vulkanox ® 4010NA: | N-isopropyl-N'-phenyl-p-phenylene-diamine |
| Vulkanox ® HS: | Poly-2,2,4-trimethyl-1,2-dihydro-quinoline |
| Protektor ® G35: | Protective ozone wax |
| V 480: | Bis(2-ethylamino-4-diethylamino-s-triazine-6-yl) tetrasulfide |
| V 675: | Bis(2,4-methylthio-s-triazine-6-yl)-polysulfide (x = 4) |

EXAMPLE 3

Comparison of the rubber-technology properties of bis(2,4-methylthio-s-triazine-6-yl) polysulfide (V 675) with those of bis(2-ethylamino-4-diethylamino-s-triazine-6-yl) tetrasulfide (V 480) in natural rubber

| RSS 1 | 100 | 100 |
|---|---|---|
| CORAX N 220 | 50 | 50 |
| ZnO RS | 5 | 5 |
| Stearic acid | 2 | 2 |
| Naftolen ZD | 3 | 3 |
| Vulkanox 4010NA | 2.5 | 2.5 |
| Vulkanox HS | 1.5 | 1.5 |
| Protektor G35 | 1 | 1 |
| V 480 | 3.5 | — |
| V 675 | — | 3.1 |
| Sulfur | 0.3 | 1 |
| Vulcanization temperature: 160° C. | | |
| Vulcanizate data at 160° C., T$_{95}$% | | |
| Vulcanization time (min) | 15 | 15 |
| t$_{10}$% (min) | 3.0 | 4.2 |
| t$_{80}$%–t$_{20}$% (min) | 3.8 | 2.4 |
| t$_{90}$%–t$_{10}$% (min) | .12.7 | 5.2 |
| MS t$_5$ 130° C.) (min) | 3.6 | 9.7 |
| MS t$_{35}$ (130° C.) (min) | 6.2 | 13.1 |
| Tensile strength (MPa) | 21.2 | 21.9 |
| Modulus 300% (MPa) | 10.1 | 10.4 |
| Tear resistance (N/mm) | 21 | 30 |

EXAMPLE 4

Reversion stability of N 220-filled SBR accelerated with bis(2,4-methylthio-s-triazine-6-yl) polysulfide (V 675) in comparison to the same rubber accelerated with bis(2-ethylamino- 4-diethylamino-s-triazine-6-yl)tetrasulfide (V 480)

| Buna | 100 | 100 |
|---|---|---|
| CORAX N 220 | 50 | 50 |
| ZnO RS | 5 | 5 |
| Stearic acid | 2 | 2 |
| Naftolen ZD | 3 | 3 |
| Vulkanox 4010NA | 2.5 | 2.5 |
| Vulkanox HS | 1.5 | 1.5 |
| Protektor G35 | 1 | 1 |
| V 480 | 1 | — |
| V 675 | — | 2 |
| Sulfur | 1.8 | 2.5 |
| vulcanization temperature: 170° C. | | |
| Reversion: | | |

| $\frac{D_{max} - D(max + 60')}{D_{max} - D_{min}}$ (%) | 8.3 | 3.9 |
|---|---|---|

What is claimed is:

1. A vulcanizable mixture comprising bis(2,4-organylthio-s-triazine-6-yl) polysulfides of the Formula (I)

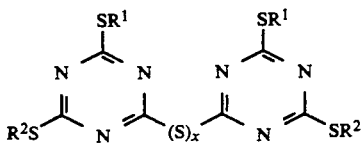

in which $R^1$, $R^2$ are identical or different and represent hydrogen, branched or unbranched alkyl with 1–4 carbon atoms, allyl, $C_3$–$C_8$-cycloalkyl, 2-hydroxyethyl, 3-hydroxypropyl, 2-hydroxypropyl, phenyl, $(S)_x$ is a polysulfide chain with 2–10 S atoms ($2 \leq x \leq 10$) and the individual sulfides are present in such concentrations that the statistical mean $x \approx 4$, as an accelerator and a vulcanizable rubber selected from the group consisting of natural rubber (NR), isoprene rubber (IR), butadiene rubber (BR), styrenebutadiene rubber (SBR), isobutylene-isoprene rubber (IIR), ethylene-propylene terpolymer (EDPM), nitrile rubber (NBR), halogen-containing rubbers, epoxidized natural rubbers (ENR), and blends of these rubbers, the amount of triazinylpolysulfides being 0.1 to 10 parts per 100 parts of rubber, and with a sulfur content of 0.1 to 10 parts by weight per 100 parts of rubber.

2. A vulcanizable mixture as set forth in claim 1 in which the amount of said bis(2,4-organylthio-s-triazine-6-yl) polysulfides is 0.1 to 5 parts by weight per 100 parts of rubber.

3. A vulcanizable mixture as set forth in claim 1 including at least one member of the group consisting of an additional accelerator, a retarder and an organosilane, the molar ratio of said bis(2,4-organyl-thio-s-triazine-6-yl) polysulfides to sulfur being 1:0.5 to 1.5.

4. A vulcanizable mixture as set forth in claim 3 which contains a retarder selected from the group consisting of N-(cyclohexylthio)-phthalimide and N-phenyl-N-(trichloromethylsulfenyl)-benzene sulfinamide.

5. A vulcanizable mixture as set forth in claim 1 which contains silica as the sole filler.

* * * * *